United States Patent [19]

von Werner

[11] Patent Number: 4,587,366

[45] Date of Patent: May 6, 1986

[54] PROCESS FOR PREPARING FLUOROALKYL-SUBSTITUTED IODOALKANES

[75] Inventor: Konrad von Werner, Halsbach, Fed. Rep. of Germany

[73] Assignee: Hoechst Aktiengesellschaft, Frankfurt am Main, Fed. Rep. of Germany

[21] Appl. No.: 663,084

[22] Filed: Oct. 19, 1984

[30] Foreign Application Priority Data

Oct. 21, 1983 [DE] Fed. Rep. of Germany ....... 3338300

[51] Int. Cl.$^4$ .................. C07C 17/28; C07C 21/18
[52] U.S. Cl. ................................. 570/172; 570/153; 570/144; 560/254; 560/260
[58] Field of Search ............ 570/172, 144, 153; 560/254, 260

[56] References Cited

U.S. PATENT DOCUMENTS

| | | | |
|---|---|---|---|
| 3,862,978 | 1/1975 | Decker et al. | 570/172 |
| 4,073,817 | 2/1978 | Jäger | 570/153 |
| 4,478,760 | 10/1984 | Blancou et al. | 570/172 |

Primary Examiner—Charles F. Warren
Assistant Examiner—John A. Sopp
Attorney, Agent, or Firm—Curtis, Morris & Safford

[57] ABSTRACT

A process is described for preparing fluoroalkyl-substituted iodoalkanes by reacting a fluorinated alkyl iodide with a substituted or unsubstituted alkene under heat in the presence of a catalyst. The catalyst is at least one metal which, in the periodic table of the elements, has one of the atomic numbers 24 to 30, 42 to 48 or 74 to 79 and is in finely divided form. The products of the process according to the invention are addition compounds of the fluorinated alkyl iodide with the substituted or unsubstituted alkene and, in known processes, can be used as useful intermediates for preparing fluorine-containing polymers, textile finishes, fire-extinguishing agents or surfactants.

6 Claims, No Drawings

PROCESS FOR PREPARING FLUOROALKYL-SUBSTITUTED IODOALKANES

The invention relates to a process for preparing fluoroalkyl-substituted iodoalkanes.

It is known to add iodoperfluoroalkanes onto the C-C double bond of alkenes which can carry various substituents. Various methods have been used for this. The purely thermal adding-on requires high temperatures, frequently leads to only moderate conversions, and generally proceeds with low selectivity, producing a mixture of various addition products.

Also known is the photochemical addition of perfluoroalkyl iodides onto alkenes, but frequently the reaction takes a long time to produce acceptable conversions and, moreover, is technically complicated and costly in terms of energy.

It is furthermore known to add perfluoroalkyl iodides onto alkenes in aprotic solvents using known catalysts which disintegrate into free radicals, catalysts such as azobis isobutyronitrile or organic peroxides. The reaction temperatures are considerably lower than in the case of the thermal addition, and frequently this form of the reaction also produces good conversions and yields of the reaction products. However, the process has the disadvantage that residues of the catalyst and in particular of its decomposition products remain in the reaction mixture and hence make it difficult to separate off the desired reaction products and to prepare them in the pure form. Moreover, the addition reaction is frequently not particularly selective, which diminishes the yield of desired products.

Finally, it is known to react perfluoroalkyl copper(I) with alkenes in an aprotic solvent (dimethyl sulfoxide), for which the reaction temperatures can again be comparatively low; admittedly, the reaction again produces mixtures of various products which make it difficult to prepare the individual products in pure form and which diminish the yield of desired products. The perfluoroalkyl copper(I) can also be formed in situ in the reaction mixture, again in the presence of an aprotic solvent (dimethyl sulfoxide), from perfluoroalkyl iodide and metallic copper; the amount of the metallic copper may be less than (for example only a third of) the stoichiometrically calculated amount. However, this form of the reaction too gives rise to an appreciable amount of byproducts, as is demonstrated by the comparative experiments given hereinafter.

We have now found a process which makes it possible to add a wholly or predominantly fluorine-substituted alkyl iodide onto alkenes in such a way as to form, in high yields, essentially only one addition product which is easily purified and reacted further to form technically interesting products. Another advantage is that the catalyst employed is easily separated off and reused.

The invention accordingly provides a process for preparing fluoroalkyl-substituted iodoalkanes by reacting a fluorinated alkyl iodide with a substituted or unsubstituted alkene under heat and under atmospheric pressure or superatmospheric pressure in the presence of a catalyst, which comprises using as said catalyst at least one metal which, in the periodic table of the elements, has one of the atomic numbers 24 to 30, 42 to 48 or 74 to 79 and is in finely divided form.

For the purposes of the invention, a "fluoroalkyl-substituted iodoalkane" is a compound which is derived from an aliphatic hydrocarbon and has no double bond at the fluoroalkyl-substituted carbon atom. Double bonds may be present elsewhere in the carbon chain, for example when one of the starting materials for the addition reaction was an alkene having two double bonds in the molecule (an alkadiene) and the fluorinated alkyl iodide was added across only one of these double bonds.

Examples of metals which are suitable for use as catalysts are cobalt, zinc, molybdenum, silver, cadmium, rhenium and osmium. Particularly good results are obtained with chromium, manganese, nickel, ruthenium, rhodium, palladium or platinum. It is also possible to use mixtures of various metals (alloys).

The metals are used in finely divided form, for example in the form of powders or chips. In particular in the case of relatively costly metals, such as ruthenium, rhodium, palladium or platinum, it is advantageous to use these in the form of deposits on finely divided, inert support material. Examples of suitable support materials are activated carbon, alumina and silica. So-called metallic sponges may also be used to good effect. The catalyst particles can be used in the form of a homogeneous dispersion in the reaction mixture or in the form of a packing (fixed bed) through which the reaction mixture flows.

The reaction is carried out within the temperature range from 80° to 180° C. Below 80° C. the yields are generally too low, while above 180° C. the yield of the desired reaction product is generally not improved further and, on the contrary, the number and quantity of the byproducts formed increases, so that it becomes more difficult to prepare the desired product in the pure form and the process becomes uneconomical. The temperature of the reaction mixture is advantageously kept at least sufficiently high for the reactants (except the catalyst) and the resulting products not to be present in solid form. The temperature range is preferably 100° to 150° C.

The process according to the invention is carried out under pressure in the event that at least one of the reactants is in the form of a gas at the chosen reaction temperature. Advantageously the process is carried out under the autogenous pressure of the reactant(s), yet it is also possible to apply a higher pressure. The pressure range in which the new process is carried out is between 0.098 and 5 MPa. The upper limit of the pressure range is essentially only dictated by economic considerations. The pressure range is preferably 0.098 to 2.5 MPa.

The duration of the reaction depends on the chosen temperature and the reactants. A duration of 1 to 50 hours is generally adequate. Below 1 hour the reaction is still incomplete, while above 50 hours there is generally no improvement in yield but an increased danger that undesirable byproducts are formed. The reaction is preferably carried out for 3 to 30 hours.

The molar ratio of the reactants (fluorinated alkyl iodide to alkene) is 10:1 to 1:10. In general, if any reactant is used in molar excess it should be the alkene, but this would increase the danger of several alkene molecules reacting with one fluorine-substituted alkyl iodide and producing less desirable products. For this reason it is necessary in some cases to use an occasionally considerable molar excess of the fluorinated alkyl iodide. The reactants are preferably used in the molar ratio of 5:1 to 1:5.

The catalyst metal is used in an amount of 0.1 to 10 mol%, of the two reacting compounds, based on whichever is used in the smaller number of moles. Below 0.1 mol% the catalyst is generally no longer sufficiently effective, while above 10 mol% no additional catalyst effect is observed. The catalyst is preferably used in an amount of 1 to 5 mol%, based on whichever of the two reacting compounds is used in the smaller number of moles.

The process according to the invention can also be carried out in the presence of solvents, but it is advantageously carried out in the absence of aprotic solvents, since the latter frequently favor the formation of undesirable byproducts. Protic solvents, surprisingly, have little if any interfering effect on the course of the reaction. It has even been found that added water (which, admittedly, is no solvent for most of the reactants) has a favorable effect on the course of the reaction. The water is preferably added to the reaction mixture in an amount of 1 to 100 mol%, based on whichever of the two reacting compounds is used in the smaller number of moles. Below 1 mol% no effect is generally observed, while above 100 mol% there is no additional effect. In particular, 3 to 30 mol%, based on whichever of the two reacting compounds is used in the smaller number of moles, is added.

Good results are obtained when the fluorinated alkyl iodide is a compound of the following formula:

$$XR_f I,$$

in which $R_f$ denotes a perfluorinated alkylene radical which is straight-chain and has 1 to 15 carbon atoms or is branched and has 3 to 15 carbon atoms or is cyclic and has 4 to 8 carbon atoms; and X denotes hydrogen, fluorine, chlorine, bromine or iodine.

The compounds in which X is fluorine or iodine are preferably used, since they are highly reactive and lead to technically interesting reaction products. For the same reasons and because they are readily accessible, preferred compounds are those in which $R_f$ denotes a perfluorinated straight-chain alkylene radical having 2 to 12 carbon atoms.

The process according to the invention can also be carried to good effect with a substituted or unsubstituted alkene of the following formula:

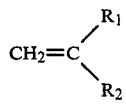

in which $R_1$ and $R_2$ can be identical or different and each denotes:

hydrogen, fluorine, chlorine, a perfluoroalkyl radical which has 1 to 12 carbon atoms and in which a fluorine atom can be replaced by hydrogen or chlorine, an alkyl radical having 1 to 20 carbon atoms, an alkenyl radical having 2 to 20 carbon atoms, an aryl radical having 6 to 10 carbon atoms or an arylalkyl radical having 7 to 12 carbon atoms, and a substituent of the last four types (alkyl, alkenyl, aryl or arylalkyl) can in turn be substituted by fluorine, chlorine, —OH or —OR', in which R' denotes an alkyl or alkylcarboxyl radical having 1 to 5 carbon atoms. $R_1$ and $R_2$ can each also denote a silyl radical which is substituted by alkyl groups containing 1 to 4 carbon atoms, by alkoxy groups containing 1 to 5 carbon atoms or by chlorine.

In particularly preferred compounds which are used, $R_2$ denotes hydrogen and $R_1$ likewise denotes hydrogen or an alkyl radical having 1 to 10 carbon atoms or an alkenyl radical having 2 to 10 carbon atoms; not only the alkyl radical but also the alkenyl radical can be substituted by —OH or —OR", in which R" denotes an alkyl or alkylcarboxyl radical having 1 to 3 carbon atoms. In equally preferred compounds, $R_2$ denotes hydrogen and $R_1$ denotes a silyl radical which is substituted by alkyl groups containing 1 to 4 carbon atoms, by alkoxy groups containing 1 to 5 carbon atoms, or by chlorine.

After the reaction has ended, the mixture is cooled down and, if it remains liquid, is freed from solid particles by filtering or centrifuging them off or by other suitable methods. The filtrate is then subjected to fractional distillation, if desired using reduced pressure. If the main fraction does not contain a sufficiently pure product, it is put through another fractional distillation. If the reaction mixture solidifies on cooling down, it is advantageously extracted with suitable low-boiling solvents, either by repeated digestion or for example in a soxhlet. Examples of suitable solvents are dichloromethane, chloroform, trichloroethylene, carbon tetrachloride, fluorinated hydrocarbons which have a low boiling point but are liquid at room temperature and which can also contain chlorine molecules, and ethers, for example diethyl ether, tetrahydrofuran or glycol dimethyl ether. All or part of the solvent is then evaporated out of the extracts and the product is purified by recrystallization, or all of the solvent is evaporated off and the product is obtained in pure form by fractional distillation, as described above. The metal or the metal-containing particles present in the filtration, centrifugation or extraction residue are cleaned if necessary, for example by washing with suitable solvents, and are reused as catalyst.

The process according to the invention produces, with high selectivity, the monoaddition compounds which are the result of the fluorinated alkyl iodide combining with the corresponding alkene and have the following formula:

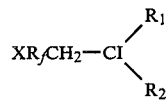

in which $R_f$, $R_1$, $R_2$ and X are as defined above. Products which are the result of the fluorinated alkyl iodide reacting with two alkenes are formed to only a minor extent and can have, for example, the following structure:

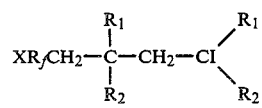

As already stated above, however, the formation of compounds of the latter formula can be kept down by using an excess of the fluorinated alkyl iodide.

The compounds produced using the new process are useful intermediates. They can be processed, for example, in line with known processes, such as, for example, that described in German Offenlegungsschrift 2,834,795, by converting the iodine atom in the molecule into a hydroxyl group. Unsaturated compounds are obtained by splitting off hydrogen iodide using alkalis, such as, for example, sodium hydroxide, potassium hydroxide, sodium carbonate or potassium carbonate, the reaction being advantageously carried out in aqueous alcoholic or pure alcoholic solutions, for example in methanol or ethanol; if water-containing media are used, the reaction is improved still further through the use of phase transfer catalysts, such as tetraalkylammonium salts or tetraalkylphosphonium salts. Compounds having double bonds at the end of the molecule are suitable as comonomers for the polymerization of fluorine-containing unsaturated hydrocarbons, for example tetrafluoroethylene. Other substances obtained from the compounds prepared in accordance with the invention serve to prepare textile finishes, for example oil- or water-repellents, as fire-extinguishing agents or as particularly stable emulsifiers, for example for electrolysis.

The following examples will explain the invention in more detail.

COMPARATIVE EXPERIMENT A AND EXAMPLES 1 TO 11

The reaction vessel is a 250 cm³ capacity V₂A stainless steel shaker autoclave which is lined with polytetrafluoroethylene. This autoclave is charged with the compounds of the formula $XR_fI$ given in the Table below, the metals (in powder form) which are given in said Table, and, if used, water, in the amounts visible in said Table. The autoclave is then sealed, is flushed first with nitrogen and then with ethylene, and is finally injected with ethylene to a pressure of 2 MPa. The autoclave is then heated up, with shaking, to the temperature indicated in the Table and is held at said temperature for the duration which is likewise indicated there, the ethylene pressure also being held constant. In other words, the ethylene consumed by the reaction is constantly replenished, so that the autoclave always contains a molar excess of ethylene over the $XR_fI$ starting compound. The metals ruthenium and platinum are used in the form of finely divided deposits on activated carbon. Said activated carbon contains about 5% by weight of ruthenium or platinum, as the case may be. The amount used is apportioned in such a way that 2 mol% of ruthenium or 1 mol% of platinum is used, based on whichever of the two reactant compounds is used in the smaller number of moles.

After the reaction has ended, the autoclave is cooled down, is let down and is opened. Its contents, if necessary after they have been melted up first, are filtered. A ¹⁹F nuclear magnetic resonance spectrum is recorded on a sample of the filtrate and is used to determine the percentage conversion, based on the starting —CF₂I groups. In Experiment A and in Examples 1 to 8 a further sample of the filtrate is analyzed by gas chromatography. The peak areas which are found in the gas chromatogram and approximately correspond to the number of moles actually formed are indicated in the Table below. In said Table, m₁ denotes the reaction product of an $XR_fI$ molecule with a molecule of the formula

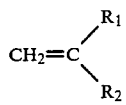

the product compound being of the following type:

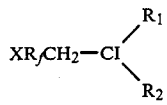

m₂ denotes the reaction product of an $XR_fI$ molecule with two molecules of a compound of the formula

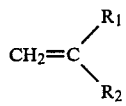

the product compound generally having the following formula:

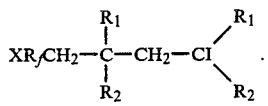

$XR_fH$ denotes a compound in which the iodine atom of the $XR_fI$ compound has been replaced by hydrogen.

In Example 9 the catalyst is not filtered off, but the catalyst-containing crude product is extracted with boiling dichloromethane in a soxhlet. Evaporating off the solvent and drying produces a colorless crystalline product which is analyzed by gas chromatography and is found to consist to 97.8% of a compound of the following formula:

ICH₂CH₂(CF₂)₄CH₂CH₂I

In this case the X in the $XR_fI$ compound used denotes a second iodine atom. The reaction with ethylene has thus produced a compound where each —CF₂I group has reacted with a molecule of ethylene. The value determined by gas chromatography was accordingly recorded in the m₁ column in the Table below.

EXAMPLE 12

The reaction vessel is a heatable 4,000 cm³ capacity V₂A steel shaker autoclave. After all the substances given in the Table below have been introduced into the autoclave in the amounts recorded in that Table, the autoclave is sealed and is flushed with nitrogen, the gas supply is discontinued and the autoclave is heated with shaking at 180° C. for 11 hours, in the course of which an autogenous pressure of 1.5 MPa becomes established in the autoclave. At the end of the reaction period, the autoclave is cooled down and is let down, the contents are filtered, and the filtrate is subjected to fractional distillation. The reaction product of one molecule of perfluorobutyl iodide with a molecule of 1,1,2-trihydro-1-perfluorohexene, this product having the formula:

C₄F₉CHI—CH₂C₄F₉ passes over at a temperature of 95° to 97° C. and under a pressure of 6.7 kPa. Under the same pressure, the next fraction passes over at 110° to 120° C. and contains the product of the reaction between a molecule of perfluoroalkyl iodide and two molecules of 1,1,2-trihydro-1-perfluorohexene, this product having the formula

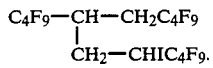

$$C_4F_9-CH-CH_2C_4F_9$$
$$\phantom{C_4F_9-}|$$
$$\phantom{C_4F_9-}CH_2-CHIC_4F_9.$$

The two fractions are weighed. The weight is used to calculate the yield as a percentage of the amount which, theoretically, could have formed in the case of complete conversion from the 1,1,2-trihydro-1-perfluorohexene, of which fewer moles were present. The value for the product of reacting a molecule of perfluorobutyl iodide with a molecule of 1,1,2-trihydro-1-perfluorohexene is listed under $m_1$ in the Table below, while the value for the product of the reaction with two molecules of 1,1,2-trihydro-1-perfluorohexene is given under $m_2$ in said Table.

EXAMPLES 13 AND 14 AND COMPARATIVE EXPERIMENTS B AND C

The reaction vessel is a heatable 250 cm³ capacity glass flask which is equipped with a stirrer, a reflux condenser, a thermometer and a gas inlet tube. Said glass flask is charged with the reactants and the catalyst given in said Table, in the amounts given therein, argon in the case of Examples 13 and 14 and in comparative Experiment B, or ethylene, in the case of comparative Experiment C, is passed in through the gas inlet tube, and the contents of the flask are raised with stirring to the temperature indicated in the Table and are maintained at that temperature for the time likewise indicated in said Table. In Examples 13 and 14 the reaction mixture is refluxed at the boiling point, which rises in the course of time. At the end of the reaction in Examples 13 and 14 the mixture is cooled down somewhat and is filtered. The $^{19}F$ nuclear magnetic resonance spectrum is recorded on samples of the filtrate, and the composition of the samples is determined by gas chromatography. From the values found, the selectivity of the reaction with respect to the formation of the monoaddition product is 94.8% in Example 13 and 96.6% in Example 14. In both cases, the bulk of the filtrate is subjected to a short-path distillation in vacuo. The following observations were made:

Example 13: the main fraction passes over at 116° C. and under 133 Pa and comprises pure $C_8F_{17}CH_2CHIC_6H_{13}$; yield: 85.5% of the theoretical amount, based on converted $C_8F_{17}I$.

Example 14: the main fraction passes over at 130° C. and under 1.87 kPa and comprises pure $C_6F_{13}CH_2CHICH_2OCOCH_3$; yield: 75.9% of the theoretical amount, based on converted $C_6F_{13}I$.

In comparative Experiments B and C the reaction mixture is cooled down at the end of the reaction period and a crude product is subjected to $^{19}F$ nuclear magnetic resonance spectroscopy. The reaction mixture is then suspended in 30 cm³ of diethyl ether and 100 cm³ of water, the suspension is filtered, and the ether-containing phase is separated off and extracted with water to remove any residual dimethyl sulfoxide present and is analyzed by gas chromatography. The values found are shown in the Table below. The selectivity of the reaction with respect to the formation of the monoaddition product is 67.2% in the case of comparative Experiment B and 58.3% in the case of comparative Experiment C. The symbols in the Table below have the following meanings:

I = Mixture of various perfluoroalkyl iodides of the following chain length distribution: 37.5% by weight of $C_6$, 37.9% by weight of $C_8$, 17.5% by weight of $C_{10}$ and 6.3% by weight of $C_{12}$.
II = 1-Iodoperfluorobutane
III = 1,4-Diiodoperfluorobutane
IV = 1-Iodoperfluorooctane
V = 1-Iodoperfluorohexane
a = Ethylene, $CH_2=CH_2$
b = 1,1,2-Trihydro-1-perfluorohexene, $CH_2=CH-C_4F_9$
c = Chloroethene (vinyl chloride)
d = 1,1-Difluoroethene (vinylidene fluoride)
e = 1-Octene
f = 2-Propen-1-ol acetate (allyl acetate).

TABLE

| Comparative experiment Example No. | $XR_fI$ | mol | $CH_2=C\begin{smallmatrix}R_1\\R_2\end{smallmatrix}$ | mol | Metal Mol-%[2+] | Water Mol-%[2+] | Temp. °C. | Pressure MPa | Duration h | Conversion %[3+] | $m_1$ | $m_2$ | Product properties (peak area %)[4+] $XR_fI$ | $XR_fH$ |
|---|---|---|---|---|---|---|---|---|---|---|---|---|---|---|
| A | I | 0.2 | a | >0.2 | — | — | 190 | 2 | 11 | 91 | 83.8 | 1.2 | 9.0 | 5.5 |
| 1 | I | 0.2 | a | >0.2 | Zn 2 | — | 130 | 2 | 8.5 | 100 | 96.1 | 3.5 | — | 0.3 |
| 2 | I | 0.2 | a | >0.2 | Cr 2 | — | 145 | 2 | 6 | 92.1 | 90.5 | 1.3 | 7.9 | 0.3 |
| 3 | I | 0.2 | a | >0.2 | Ni 2 | — | 125 | 2 | 12 | 98.6 | 97.5 | 1.2 | 0.9 | 0.5 |
| 4 | I | 0.2 | a | >0.2 | Ag 2 | — | 125 | 2 | 11 | 95.5 | 93.8 | 1.3 | 4.0 | 0.8 |
| 5 | I | 0.2 | a | >0.2 | Re 2 | — | 135 | 2 | 12 | 92.3 | 90.5 | 1.8 | 7.1 | 0.4 |
| 6 | I | 0.2 | a | >0.2 | Ru[+] 2 | — | 100 | 2 | 11 | 84.8 | 83.7 | 0.2 | 15.2 | 0.9 |
| 7 | I | 0.2 | a | >0.2 | Pb[+] 2 | — | 90 | 2 | 4 | 78.8 | 78.4 | — | 21.2 | 0.2 |
| 8 | II | 0.4 | a | >0.4 | Ru[+] 2 | 5 | 120 | 2 | 6 | 100 | 99.4 | n.b. | n.b. | n.b. |
| 9 | III | 0.68 | a | >0.68 | Ru[+] 1 | — | 170 | 2 | 33 | 98.5 | 97.8 | n.b. | n.b. | n.b. |
| 10 | II | 0.3 | c | 0.1 | PT[+] 1 | — | 155 | n.b. | 12 | 23.9 | 22.8 | 4.9 | 72.3 | n.b. |
| 11 | II | 0.2 | d | 0.1 | Ru[+] 2 | 20 | 150 | n.b. | 12 | 21.2 | 36.3 | 2.8 | 60.3 | n.b. |
| 12 | II | 6 | b | 1 | Ru[+] 2 | 5 | 180 | 1.5 | 11 | 35 | 79.9[5+] | 8.3[5+] | n.b. | n.b. |
| 13 | IV | 0.1 | e | 0.15 | Ni 2 | 10 | 122–170 | 0.1 | 7 | 98 | 92.6 | 5.1[6+] | 2.3 | n.b. |
| 14 | V | 0.2 | f | 0.2 | Cu 5 | 50 | 85–100 | 0.1 | 5.5 | 69.7 | 68.1 | 2.4 | 29.5 | n.b. |
| B | IV | 0.1 | e | 0.1 | Cu 5 | 7[++] | 110 | 0.1 | 5 | 41.3 | 28.3 | 11.3[6+] | 57.9 | 2.5 |

TABLE-continued

| Comparative experiment Example No. | $XR_fI$ | mol | 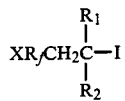 | $R_2$ | mol | Metal Mol-%[2+] | Water Mol-%[2+] | Temp. °C. | Pressure MPa | Duration h | Conversion %[3+] | $m_1$ | Product properties (peak area %)[4+] | | |
|---|---|---|---|---|---|---|---|---|---|---|---|---|---|---|---|
| | | | | | | | | | | | | | $m_2$ | $XR_fI$ | $XR_fH$ |
| C | IV | >0.1 | a | | 0.1 | Cu 66[8+] | 7+ | 110 | 0.1 | 11 | 98 | 57.0 | 40.8[9+] | 1.9 | n.b. |

[+] on activated carbon
[2+] based on whichever of the two reactant compounds is used in the smaller number of moles
[3+] based on the $-CF_2I$ groups present in the $XR_fI$ compound
[4+] determined by gas chromatography
[5+] yield in % of the theoretical amount, based on starting compound b
[6+] no double-addition product, but a mixture of $C_8F_{17}CH_2-CH=CH-C_5H_{11}$ and $C_8F_{17}CH_2CH_2CH_2C_5H_{11}$
[7+] no water used, but 50 cm³ of dimethyl sulfoxide
[8+] this corresponds to ½ of the amount which, stoichiometrically, is necessary for forming $R_fCu + CuI$
[9+] various byproducts. No addition compound of 2 molecules of ethylene onto $C_8F_{17}I$ is detectable.
n.b. not determined.

I claim:

1. A process for preparing a monoaddition compound of the formula $$XR_fCH_2\overset{R_1}{\underset{R_2}{C}}-I$$

in which
  $R_f$ denotes a perfluorinated alkylene radical which is straight-chain and has 1 to 15 carbon atoms, which is branched and has 3 to 15 carbon atoms or which is cyclic and has 4 to 8 carbon atoms,
  X denotes hydrogen, fluorine, chlorine, bromine or iodine, and
  $R_1$ and $R_2$ are identical or different and each denotes: hydrogen, fluorine, chlorine, a perfluoroalkyl radical having 1 to 12 carbon atoms, a perfluoroalkyl radical having 1 to 10 carbon atoms and in which a fluorine atom is replaced by hydrogen or chlorine, an alkyl radical having 1 to 20 carbon atoms, an alkenyl radical having 2 to 20 carbon atoms, an aryl radical having 6 to 10 carbon atoms, an arylalkyl radical having 7 to 12 carbon atoms, or a substituent of the last four types substituted by flourine, chlorine, —OH or —OR', in which R' denotes an alkyl or alkylcarboxyl radical having 1 to 5 carbon atoms, which comprises reacting a compound of the formula $XR_fI$ with a compound of the formula

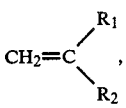

wherein X, $R_f$, $R_1$ and $R_2$ are as defined above, under heat and under atmospheric pressure or superatmospheric pressure in the presence of 0.1 to 10 mol%, based on whichever of the two reacting compounds is used in the smaller number of moles, of at least one metal catalyst which, in the periodic table of the elements, has one of the atomic numbers 24 to 30, 42 to 48 or 74 to 79 and is in finely divided form.

2. The process as claimed in claim 1, wherein the catalyst is chromium, manganese, nickel, ruthenium, rhodium, palladium or platinum.

3. The process as claimed in claim 1, wherein the catalyst metal is present on a finely divided, inert support material.

4. The process as claimed in claim 1, wherein the reaction is carried out at a temperature of 80° to 180° C.

5. The process as claimed in claim 1, wherein the reaction is carried out at a temperature of 100° to 150° C.

6. The process as claimed in claim 1, wherein water is added to the reaction mixture in an amount of 1 to 100 mol%, based on whichever of the two reacting compounds is used in the smaller number of moles.

* * * * *